United States Patent
Stolz

(10) Patent No.: US 8,034,012 B2
(45) Date of Patent: Oct. 11, 2011

(54) NAIL BRACE APPLICATOR

(76) Inventor: Bernd Stolz, Amberg (DE)

( * ) Notice: Subject to any disclaimer, the term of this patent is extended or adjusted under 35 U.S.C. 154(b) by 276 days.

(21) Appl. No.: 12/372,891

(22) Filed: Feb. 18, 2009

(65) Prior Publication Data

US 2009/0211197 A1 Aug. 27, 2009

(30) Foreign Application Priority Data

Feb. 21, 2008 (DE) .......................... 10 2008 010 442

(51) Int. Cl.
*A61F 5/00* (2006.01)
(52) U.S. Cl. ............................................ 602/30; 602/31
(58) Field of Classification Search ............ 602/23, 602/30–31; 128/893–894
See application file for complete search history.

(56) References Cited

U.S. PATENT DOCUMENTS

| | | | | |
|---|---|---|---|---|
| 1,708,716 A | * | 4/1929 | Andersen ........................ | 602/31 |
| 2,567,601 A | * | 9/1951 | Heinold et al. ................ | 602/31 |
| 2,632,441 A | * | 3/1953 | Tuve .............................. | 602/31 |
| 3,799,160 A | * | 3/1974 | Hahn ............................. | 602/31 |
| 5,938,030 A | | 8/1999 | Stolz | |

FOREIGN PATENT DOCUMENTS

| | | |
|---|---|---|
| DE | 37 08 811 A1 | 5/1990 |
| DE | 296 10 208 U1 | 8/1999 |
| EP | 0 282 645 B1 | 5/1990 |

* cited by examiner

*Primary Examiner* — Michael A. Brown
(74) *Attorney, Agent, or Firm* — Browdy and Neimark, PLLC

(57) ABSTRACT

The nail brace applicator serves for the application of a strip-shaped and leaf-spring-like nail brace onto a nail of a toe or finger. It comprises an elongated main body extending in a longitudinal direction, having a first end face extending approximately perpendicular to the longitudinal direction and having a first application zone with a first application surface formed by the first end face. Additionally, the nail brace applicator comprises a mounting element for releasably mounting the nail brace to be applied on the first application surface.

12 Claims, 2 Drawing Sheets

NAIL BRACE APPLICATOR

BACKGROUND OF THE INVENTION

1. Field of the Invention

The invention relates to a nail brace applicator for applying a strip-shaped and leaf-spring-like nail brace onto a nail of a toe or finger.

2. Background Art

Such nail braces are known from EP 0 282 645 B1. This nail brace in the form of a leaf-spring-like strip is used to lift the sides of an overly curved nail. The nail brace is a strip made of a resilient plastic material. It is glued by means of a rapid cure adhesive along its entire brace length onto the nail that is to be corrected.

EP 0 282 645 B1 also describes a nail brace applicator that is used for the defined positioning and fixing of the nail brace. This special tool has approximately the shape of a pencil whose one pointed end is provided with an inwardly extending concave recess. This end is used to press the nail brace onto the nail that is to be corrected. The other end is designed as a spatula for applying the adhesive. This nail brace applicator has proven very effective in practice. Nonetheless, even with the use of this nail brace applicator, the application of the nail brace still requires a certain amount of dexterity and possibly the use of an additional tool, e.g. a pair of tweezers, in order not to come into contact with the rapid cure adhesive.

SUMMARY OF THE INVENTION

It is, therefore, the object of the invention to present a nail brace applicator of the type described at the outset that further simplifies the application of the nail brace to the nail that is to be corrected.

To meet this object, a nail brace applicator is presented comprising an elongated main body extending in a longitudinal direction, having a first end face extending approximately perpendicular to the longitudinal direction and having a first application zone with a first application surface formed by the first end face, and a mounting element for releasably mounting, on the first application surface, the nail brace that is to be applied.

The inventive nail brace applicator is characterized in that it is particularly easy to manipulate. In particular, one longitudinal end of the nail brace can be fixed without difficulty on the application surface by means of the mounting element, wherein this mounting is only of a temporary nature and easily released. A plug-type connection is one option, for example. Only after that does the nail brace come into contact with the adhesive, either through direct application of the adhesive onto its unmounted and consequently freely accessible partial area, or through placement onto the adhesive-coated nail.

Once the unmounted, freely accessible partial area of the nail brace is fixed on the nail by the effect of the adhesive force the mounting of the nail brace on the application surface is released, e.g. by simply pulling the nail brace applicator off to the side. Afterwards the partial area of the nail brace that was initially not accessible for gluing because of the mounting may then be glued to the nail as well. Pressing the nail brace onto the nail and final fixing of the same on the nail take place by means of the nail brace applicator in each case. Its elongated main body serves as an easy-to-grasp handle during the application process, thereby preventing the fingers of the person performing the application (e.g. a chiropodist) from coming into contact with the quick-setting adhesive.

The portion of the nail brace applicator that adjoins the first application zone forms, in particular, a handle element.

Furthermore, because of the grasping function that is incorporated in the inventive nail brace applicator, no second tool is needed, in particular no tweezers. All movements can be performed without any special manual dexterity, using only the inventive nail brace applicator.

Advantageous is a variant in which the, in particular, rectangular first application surface is matched in at least one geometric dimension to a corresponding geometric dimension of the nail brace that is to be applied. To this effect it is preferably provided that the first application surface has an application surface length that is substantially equal to a brace length of the nail brace that is to be applied. The application surface length in this context is in particular equal to the width of the main body at the first end face. In this manner the nail brace applicator can be used for measuring the nail width of the nail that is to be treated and for selecting the proper brace length. Furthermore, it is advantageous if the first application surface has an application surface width that is substantially equal to a brace width of the nail brace that is to be applied. The application surface width in this context is in particular equal to the thickness (or depth) of the main body at the first end face. This results in an improved control of the application. It is possible to see and examine precisely where the nail brace is being placed. This allows for readjustments within the short amount of time until the adhesive sets.

According to another advantageous variant, the first application zone of the main body has, in a corner region in which the first end face and a first side wall of the main body meet, a mounting projection, and the mounting element is designed as a flexible, in particular rubber-elastic sleeve, for example in the form of a ring-shaped closed band or rubber ring. The sleeve can be slipped onto the mounting projection in such a way that, in its slipped-on state, it also encloses one longitudinal end of the nail brace that was placed on the application surface and is to be applied. This achieves, in a simple manner, an easily releasable and nonetheless sufficiently stable mounting of the nail brace on the application surface. The one longitudinal end of the nail brace can simply be inserted alongside the application surface into the flexible sleeve. This, accordingly, results in a kind of plug-type connection.

The mounting projection is formed in particular by means of a notch that is provided on the first side wall extending away from the first end face. The notch is disposed in particular adjacent to, i.e. near the end face and extends into the main body preferably parallel to the first end face. The mounting projection that is designed in this way can be produced inexpensively. The notch may be sawed, for example, or punched out.

Furthermore, the notch may preferably be disposed at a distance from the end face that is approximately equal to a thickness of the main body.

The mounting projection then has an approximately square cross section onto which the flexible sleeve can be slipped particularly easily. At the same time a good clamping effect is provided in this manner for a mounted nail brace.

In an additional advantageous embodiment the first application zone of the main body has, on a second side wall extending away from the first end face, adjoining the first end face, an in particular curved first recess. If the nail brace is to be pressed onto a lateral outer edge of a highly curved toenail the nail brace applicator may need to be tilted by a significant degree toward the adjacent toe. The longitudinal direction of the nail brace applicator then forms an acute angle with the plane in which the toes are located or, in the extreme case, is even oriented parallel to this plane. The curved recess permits a wide tilting range of the nail brace applicator in this respect, in such a way that it prevents a premature collision of the nail brace applicator with the adjacent toe. The recess provides a free space for the adjacent toe.

Additionally preferred is a variant in which the main body has a second application zone that comprises, as a second application surface, a second end face located opposite the first end face, with the respective application surface lengths of the first and second application surface being different from each another. Apart from the geometric dimensions the second application zone is designed identical to the first application zone, i.e. the design features are identical in each case. One nail brace applicator can thus be used for the application of nail braces with two different strip lengths. This reduces the number of nail brace applicators that need to be provided for the various brace lengths.

Additionally it is advantageous if the main body consists of a material that does not enter into an adhesive bond with the adhesive that is used in the application of the nail brace. This prevents the occurrence of an inadvertent firmly adhering connection between the nail brace applicator and the nail brace during the application process. The connection is then defined only by the mounting element and remains releasable as desired. The main body consists, for example, of a polyethene (PE) plastic material. This plastic material does not enter into an adhesive bond in particular with the cyanacrylate adhesive that is often used as an instant-set adhesive or fast adhesive in this context.

According to an additional advantageous variant the main body has a main body color with a color contrast from a brace color of the nail brace that is to be applied. This facilitates the application. In this manner it is easier to control how the nail brace being applied is positioned at any particular time.

Additional characteristics, advantages and details of the invention will become apparent from the following description of an exemplary embodiment in conjunction with the drawing.

DESCRIPTION OF THE PREFERRED EMBODIMENT

Figure 1:
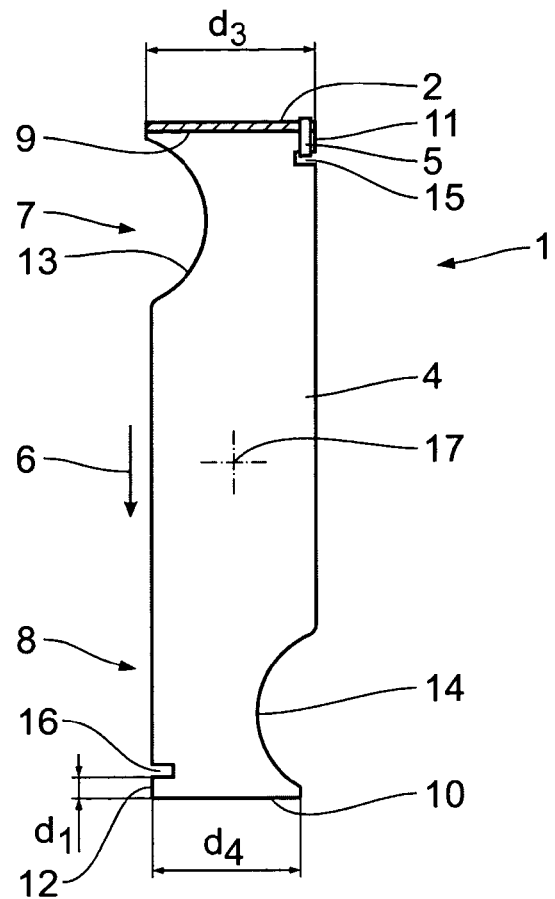
FIG. 1 shows, in a side view, an exemplary embodiment of a nail brace applicator with a nail brace mounted on an application surface.

Elements that correspond to each other are denoted by the same reference numerals in FIGS. 1 through 5.

Figure 2:
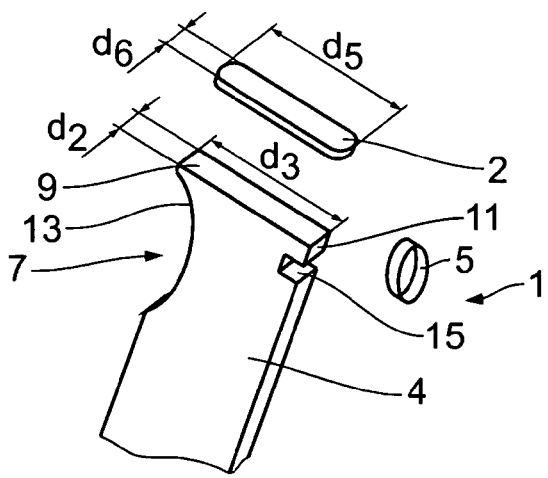
FIG. 2 shows a detail of the nail brace applicator and nail brace according to FIG. 1 in a perspective exploded view.
Figure 3:
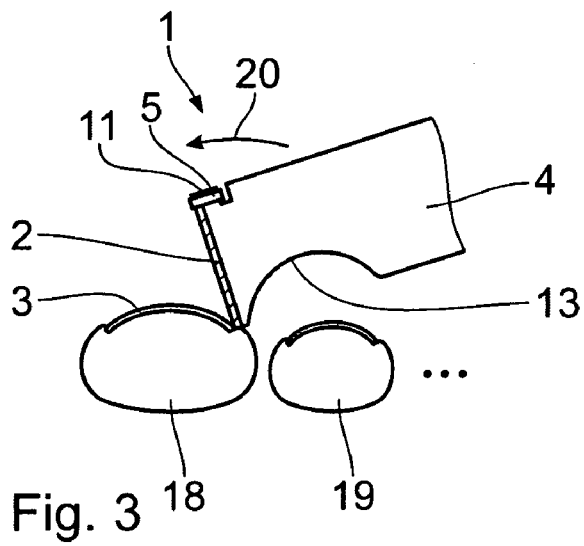
FIGS. 3 through 5 show the sequence of an application of a nail brace onto a toenail using the nail brace applicator of FIG. 1.
Figure 4:
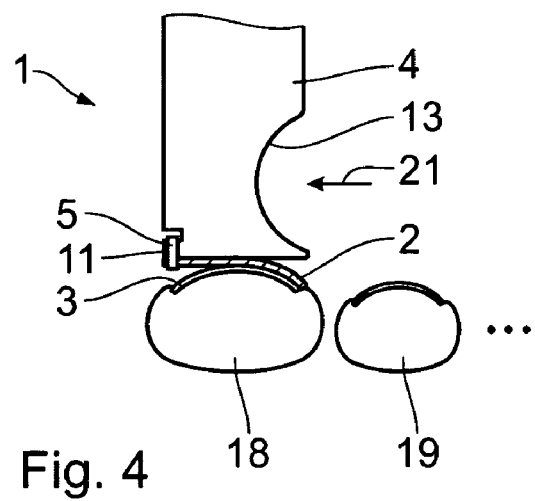
Figure 5:
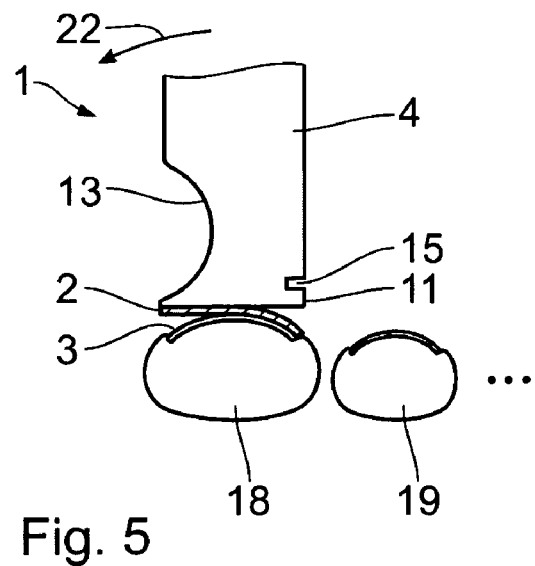

FIGS. 1 and 2 show an exemplary embodiment of a nail brace applicator 1 for application of a strip-shaped and leaf-spring-like nail brace 2 onto a toenail 3 (see FIGS. 3 through 5.) The nail brace applicator 1 comprises an elongated main body 4 of polyethene (PE) and a flexible rubber-elastic sleeve 5 that is designed in the style of a rubber ring.

The main body 4 has a rectangular basic shape, the longest geometric dimension (=length) of which extends in a longitudinal direction 6. Adjoining its two end faces that extend approximately perpendicular to the longitudinal direction 6 in each case, the main body has an application zone 7 and 8 in each case. The latter include, in addition to the respective end faces that are designed as application surfaces 9 and 10, also a mounting projection 11 and 12 in each case on one side wall of the main body 4, as well as a curved—in the exemplary embodiment circle-arc shaped—recess 13 and 14 in each case on the other side wall of the main body 4. Each of the mounting projections 11 and 12 adjoins one of the application surfaces 9 and 10 in each case and is created by a respective notch 15 or 16 that extends starting from the side wall of the main body 4 in parallel with the application surface 9 and 10 in each case into the main body 4. A distance $d_1$ of the respective notch 15 or 16 from the respective associated application surface 9 or 10 is approximately equal in size to a thickness $d_2$ of the main body 4, with $d_2$ at the same time also representing an application surface width of the application surface 9 or 10, respectively. This results in an approximately square cross section in each case (see FIG. 2) for the mounting projections 11 and 12 that are designed as integral components of the main body 4.

The sleeve 5 forms a mounting element for releasably mounting the nail brace applicator 2 on the application surface 9. It can be slipped onto the mounting projection 11 and also pulled off from the same. In the slipped-on state (see FIG. 1) the sleeve 5 encloses, besides the mounting projection 11, also one longitudinal end of the nail brace 2 that was placed on the application surface 9, thereby releasably fixing the nail brace 2 on the main body 4.

Apart from the extension of the application surfaces 9 and 10 the application zones 7 and 8 are substantially identical in their design and in particular also designed mirror-symmetrical relative to a center 17 of the main body 4. Because of the substantially uniform design of the application zones 7 and 8, FIGS. 2 through 5 depict in each case, by way of example, only a detail of the nail brace applicator 1 that includes the application zone 7.

The application surface lengths $d_3$ and $d_4$ of the respective application surfaces 9 and 10, however, are different from each other. The respective application surface lengths $d_3$ and $d_4$ correspond to a width of the main body 4 in the region of the respective end faces (=application surfaces 9 and 10). In the exemplary embodiment the application surface length $d_3$ is 24 mm and therefore greater than the application surface length $d_4$ that has an extension of only 22 mm. Other length combinations $d_3/d_4$, such as e.g. 20 mm/18 mm and 16 mm/14 mm, however, are also possible in principle.

The respective application surface 9 and 10 is matched in its extension to the nail brace 2 that is to be applied in each case. The reason being that the nail brace 2 may have, depending on the toenail that is to be corrected, different dimensions. This applies in particular to its brace length $d_5$ that varies depending on the application. There are nail braces 2, for example, with a strip length $d_5$ of, for example 24 mm, 22 mm, 20 mm, 18 mm, 16 mm and 14 mm. The respective application surface length $d_3$ and $d_4$ corresponds in each case to one of these strip lengths $d_5$ of the nail braces 2 to be applied. Likewise, the application surface width $d_2$ matches a brace width $d_6$ of the nail brace 2 that is to be applied. Additionally, the application surface 9 and 10 is flat in each case and accordingly matched also in this regard to the likewise flat shape of the nail brace 2 in its not yet applied state. The curvature of the nail brace 2 is created only during its application.

The nail brace 2 is designed as a leaf-spring-like strip consisting of a resilient plastic material, preferably of a glass-fiber reinforced duroplast. Such a plastic material retains its resilience, not least because of the glass-fiber reinforcement, when it is designed as a very thin strip. The restoring action that is exerted onto the toenail 3 by a nail brace 2 affixed on the same will not start to decrease shortly after the nail brace 2 has been affixed. In the shown exemplary embodiment the nail brace 2 consists of the glass-fiber reinforced duroplast HGW 2372.4. The strip is produced by punching it out from a corresponding sheet material and has rounded longitudinal ends (see FIG. 2) to prevent pressure points. The nail brace 2 is less than 0.5 mm thick.

The use of and special characteristics and advantages of the nail brace applicator 1 will be described in detail below, with reference made in particular to the illustrations of FIGS. 3 and 5.

The nail brace 2 is intended to correct the toenail 3 that is overly curved in particular in the area of its lateral outer edges and accordingly is not only unsightly but also causes pain.

FIGS. 3 and 5 show the sequence of an application of the nail brace 2 onto the toenail 3 with the aid of the nail brace applicator 1. Shown are the toe to be treated 18 as well as the adjacent toe 19 in a view from the front.

The nail brace applicator 1, however, finds application already before the actual application process shown in FIGS. 3 through 5. The reason being that it may advantageously also be used for determining the brace length $d_5$ that is required for the toenail 3 to be treated. Since the application surface length $d_3$ or $d_4$ is equal in each case to one of the available brace lengths $d_5$, the nail brace applicator 1 may be used for measuring the toenail 3 that is to be treated. Based on the respective application surface length $d_3$ or $d_4$ that presents the best match for the width of the toenail 3 to be treated the nail brace 2 is selected that is best suited in this case. From the multitude of available nail braces 2 with different brace lengths $d_5$ in each case, the one that has e.g. a distance of approximately 1 mm from the lateral nail wall is selected.

The proper size nail brace 2 that was selected in this manner is fixed by means of the sleeve 5 on the application surface 9 of the proper nail brace applicator 1 for this brace length $d_5$ in such a way that it is inserted with one of its longitudinal ends in-between the sleeve 5 and the application surface 9. Alternatively, the nail brace 2 may also be placed onto the application surface 9 first, in order to then slip the sleeve 5 onto the mounting projection 11 and positioned nail brace 2.

After that, the nail brace 2 is coated on the surface facing away from the nail brace applicator 1 in the region of the unmounted half with a rapid cure adhesive. Alternatively, the adhesive application may also take place on the toenail 3 being treated.

After that, the nail brace applicator 1 with the mounted nail brace 2 is positioned, as shown in FIG. 3, against a lateral outer edge of the toenail 3 to be treated, in such a way that the unmounted longitudinal end of the nail brace 2 comes into contact with the toenail 3 first. In the process the nail brace applicator 1, depending on the anatomic conditions, may need to be tilted quite significantly toward the adjacent toe 19. In order to permit even a very pronounced tilting of this kind without resulting in a collision with the adjacent toe 19, the recess 13 is provided on the side wall of the nail brace applicator 1 that faces the adjacent toe 19 in this situation. The recess 13 provides a free space for the adjacent toe 19 (see FIG. 3).

The longitudinal end of the nail brace 2 is pressed onto the lateral outer edge of the toenail 3 by means of the nail brace applicator 1 until the rapid cure adhesive has set sufficiently for the nail brace 2 to be secured to the toenail 3 in that area. This is followed by a first tilting movement of the nail brace applicator 1 toward the center of the toenail 3, i.e. in the direction of the arrow 20 (see FIG. 3). Once it has reached this center position, the nail brace 2 is again pressed in this position against the toenail 3 by means of the nail brace applicator 1 until the effect of the adhesive force has set in here as well (see FIG. 4).

Afterwards the mounting connection between the nail brace applicator 1 and the nail brace 2 that is already partly applied on the toenail 3 is released in such a way that the nail brace applicator 1 is pulled off to the side in the direction of the longitudinal end of the nail brace 2 that has not yet been fixed in place. This pulling-off movement is indicated in FIG. 4 by the arrow 21. The sleeve 5 is pulled off along with the nail brace applicator 1 from the longitudinal end of the nail brace 2 that was mounted until then, thereby rendering this longitudinal end as well freely accessible for the now following gluing process.

If required, rapid-cure adhesive is then reapplied in the not yet glued region of the nail brace 2 or toenail 3. The nail brace applicator 1, after having been pulled off, is turned about its longitudinal center axis by 180° and again placed on the nail brace 2 in the center position. This is followed by a second tilting movement of the nail brace applicator 1 toward the not yet attached lateral outer edge of the toenail 3, i.e. in the direction of the arrow 22 (see FIG. 5.) There, the nail brace 2 is again pressed by means of the nail brace applicator 1 onto the toenail 3 in this position until the adhesive force has set in here as well. This essentially concludes the application process.

The nail brace applicator 1 significantly facilitates the application of the nail brace 2. It may be used in the process as a universal tool for measuring and application. Furthermore, when a nail strip applicator 1 is used, this largely guarantees that the fingers of the treating chiropodist do not come into direct contact with the rapid cure adhesive.

If required, a final sealing of the applied nail brace 2 may be performed in particular in the region of its lateral edges. The rapid cure adhesive, for example, that is used in the actual application may be used here as well. The seal coat dries after approximately three minutes. The nail brace 2 that is now completely fixed in place in this manner then barely protrudes beyond the toenail 3 and thus does not significantly inconvenience its wearer.

If a higher correcting force should prove necessary for particularly thick nails or nails with a particularly pronounced curvature, two nail braces 2 can easily be arranged parallel to each other. On the other hand, it is also possible to reduce a potentially unnecessarily strong correcting force in such a way that the nail brace 2 is ground thinner, e.g. by means of a co-rundum grinding stone. It is thus possible to provide for very individualized adjustments of the correcting force.

What is claimed is:

1. A nail brace applicator for application of a strip-shaped and leaf-spring-like nail brace (2) onto a nail (3) of a toe or finger, comprising
    a) an elongated main body (4) extending in a longitudinal direction (6), having a first end face extending approximately perpendicular to the longitudinal direction (6) and having a first application zone (7) with a first application surface (9) formed by the first end face, and
    b) a mounting element (5) for releasably mounting the nail brace (2) to be applied on the first application surface (9),
    wherein the first application zone (7) of the main body (4) has, in a corner region in which the first end face and a first side wall of the main body (4) meet, a mounting projection (11) and the mounting element is designed as a flexible sleeve (5) that can be slipped onto the mounting projection (11) in such a way that, in its slipped-on state, it also encloses one of the longitudinal ends of the nail brace (2) that is placed on the application surface (9) and to be applied.

2. A nail brace applicator according to claim 1, wherein the first application surface (9) has an application surface length ($d_3$) that is equal to a brace length ($d_5$) of the nail brace (2) that is to be applied.

3. A nail brace applicator according to claim 1, wherein the first application surface (9) has an application surface width ($d_2$) that is equal to a brace width ($d_6$) of the nail brace 2 that is to be applied.

4. A nail brace applicator according to claim 1, wherein the flexible sleeve (5) is rubber-elastic.

5. A nail brace applicator according to claim 1, wherein the mounting projection (11) is formed by means of a notch (15) on the first side wall extending away from the end face.

6. A nail brace applicator according to claim 5 wherein the notch (15) is disposed at a distance ($d_1$) from the end face that is approximately equal to a thickness ($d_2$) of the main body (4).

7. A nail brace applicator according to claim 1, wherein the first application zone (7) of the main body (4) has, at a second side wall extending away from the first end face, and adjoining the first end face, a first recess (13).

8. A nail brace applicator according to claim 7, wherein the first recess (13) is curved.

9. A nail brace applicator according to claim 1, wherein the main body (4) has a second application zone (8) that comprises, as a second application surface (10), a second end face located opposite the first end face, wherein the respective application surface lengths ($d_3$, $d_4$) of the first and second application surface (9, 10) are different from each other.

10. A nail brace applicator according to claim 1, wherein the main body (4) consists of a material that does not enter into an adhesive bond with the adhesive used in the application of the nail brace (2).

11. A nail brace applicator according to claim 1, wherein the material of the main body (4) is a polyethene (PE) plastic material.

12. A nail brace applicator according to claim 1, wherein the main body (4) has a main body color that contrasts from a brace color of the nail brace (2) that is to be applied.

* * * * *